United States Patent
Childs

[11] Patent Number: 5,174,305
[45] Date of Patent: Dec. 29, 1992

[54] PORTABLE DIALYSIS BAG PROTECTIVE SKIRT

[76] Inventor: Yvonne M. Childs, 5456 Harper's Farm Rd., B-1, Columbia, Md. 21044

[21] Appl. No.: 653,893

[22] Filed: Feb. 12, 1991

[51] Int. Cl.⁵ .......................... A61F 5/44; A61F 5/37; A41D 1/14
[52] U.S. Cl. .................... 128/846; 128/849; 2/211; 604/332
[58] Field of Search .............. 128/887, 888, 161, 162; 604/322, 356, 357, 393, 332; 2/47, 48, 211, 67, DIG. 5

[56] References Cited

U.S. PATENT DOCUMENTS

| | | | |
|---|---|---|---|
| 1,264,445 | 4/1918 | Schwieger | 2/211 |
| 1,846,593 | 2/1932 | Hartmann | 2/48 |
| 2,584,249 | 2/1952 | Belcher | 604/357 X |
| 2,756,751 | 7/1956 | Smith | 604/356 X |
| 2,813,530 | 11/1957 | Nunn | 604/357 X |
| 2,955,292 | 10/1960 | McKend | 2/48 |
| 3,550,590 | 12/1970 | Keilman | 128/161 |
| 4,106,125 | 8/1978 | Palumbo | 2/213 |
| 4,495,662 | 1/1985 | Miller | 2/211 |
| 4,498,200 | 2/1985 | Livingstone | 2/211 X |
| 4,559,937 | 12/1985 | Uinson | 604/356 |
| 4,709,695 | 12/1987 | Kohn et al. | 128/888 X |

Primary Examiner—Robert A. Hafer
Assistant Examiner—Brian E. Hanlon
Attorney, Agent, or Firm—Jerome J. Norris

[57] ABSTRACT

A skirt that allows a patient using a portable dialysis bag to shower without wetting the bag comprising, a skirt having a flexible waist band with an elastic disposed therein, a securing arrangement at overlapping portions of waist ends to hold the skirt about the patient's waist, and a pocket disposed on the interior side of the skirt to hold the dialysis bag. The pocket has a flap thereover that is press-fitted to effect closure between fasteners on the flap and pocket.

4 Claims, 1 Drawing Sheet

PORTABLE DIALYSIS BAG PROTECTIVE SKIRT

BACKGROUND OF THE INVENTION

1. Field of the Invention

The present invention relates to a protective skirt, and more particularly to a waterproof skirt that is capable of protecting a portable dialysis bag and the body area or opening normally connected to said bag, while the patient is in the process of taking a shower to cleanse body areas inside and outside of the skirt and not connected to said bag.

A portable dialysis bag is connected to an opening or stoma in the body area and is used to separate impurities and toxic wastes from the blood of kidney patients by means of the unequal diffusion through semipermeable membranes disposed in said bag. Because of the risk of ruining or rendering the bag inoperable due to the infusion of water, or the risk of infection if water should contaminate the bag patients with these body openings are normally advised not to shower.

2. The Prior Art

Various efforts have been made to cover a bandaged limb or body area to prevent it from getting wet so that the patient can take a shower. One approach is to place the bandaged limb in a plastic type bag and seal the open end of said bag with a rubber band; however, this arrangement does not always provide a good seal and water can accumulate in the plastic bag and damage a cast, bandage or injured area of the limb.

Another approach is disclosed in U.S. Pat. No. 2,224,871 and incudes and elongated, waterproof tubular member within which a limb is placed; said tubular member defining an integral sealing flange of an endless band of soft and elastic sheet rubber or latex that extends completely around the tubular member interior adjacent an upper end. An adequate seal is not always provided with this structure and there is no adjustability to accommodate for size differences. Further, uninjured areas of the limb which do not require protection from water must go unwashed when this member forms an effective seal.

U.S. Pat. No. 4,036,220 discloses a waterproof protective device for use on body members such as bandaged or injured portions of the trunk and limbs comprising a flexible-tubular body member enclosing means and a member securing means.

Finally, U.S. Pat. No. 4,363,317 discloses a watertight cast cover which includes an elongated tubular member having a closed lower end and an open top dimensioned to loosely receive an individual's limb.

None of these devices are sufficient to satisfy the need for a reusable waterproof means that is capable of protecting a portable parenteral solution bag or dialysis bag as well as the body opening normally connected to said bag, if a patient removes the bag from the body opening in the process of taking a shower in order to cleanse body areas outside of the waterproof means while protecting the bag and stoma or body opening from getting wet.

SUMMARY OF THE INVENTION

It is an object of the invention to provide waterproof means capable of protecting a portable dialysis bag and the body area normally connected to said bag from getting wet, while a kidney patient is in the process of taking a shower to cleanse areas inside and outside of the protective waterproof means, while preventing the bag and stoma from getting wet.

In general, the invention resolves the problem or satisfies the need by providing a protective waterproof skirt comprising: a flexible waistband of crimped and non-crimped portions having elastic means disposed therein; securing means at overlapping portions of the waist ends to hold the skirt in place around a patient's waist; and a pocket disposed on the inside of the skirt having a flap with securing means over the pocket opening to prevent any water which may enter into the skirt from getting into the pocket opening containing a portable parenteral solution bag, or dialysis bag and getting the bag wet. The non-crimped portion of the waistband also serves to prevent the area of the body that is normally attached to the bag from getting wet and thereby risking infection.

DETAILED DESCRIPTION OF THE INVENTION

Figure 1:
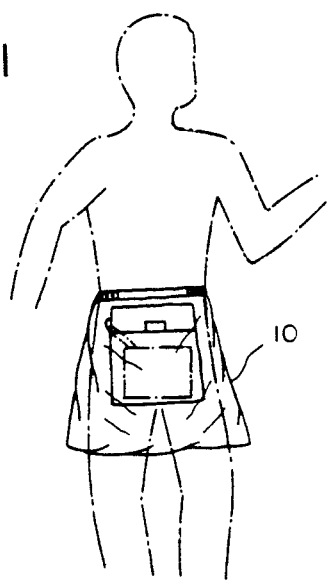
FIG. 1 is a perspective view showing a portable dialysis bag protective skirt of the invention on a patient.
Figure 2:
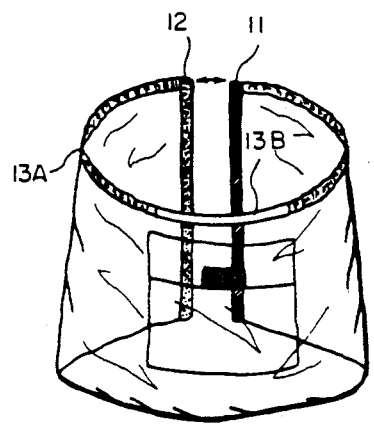
FIG. 2 is a front view of a see-through portable dialysis bag protective skirt showing rear end seam surfaces immediately before they are pressed into contact to secure the skirt and with the securing means on the inside pocket flap pressed into contact with the securing means of the pocket.
Figure 3:
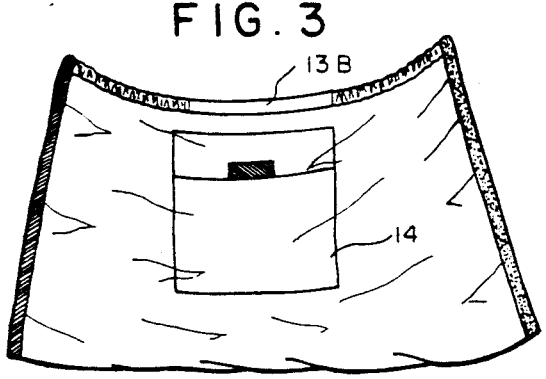
FIG. 3 is a front view of the dialysis bag protective skirt in the open position with the pocket closed.
Figure 4:
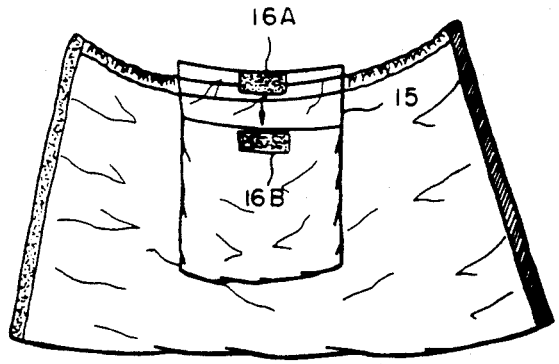
FIG. 4 is a back or inside view of the dialysis bag protective skirt showing the flap in the open or unclosed position.

The invention, as depicted in FIG. 1 shows a see-through portable dialysis bag protective skirt 10, press fitted about the waist of a patient through the use of securing means 11 and 12, which comprise interconnecting male and female fastening means, wherein one of said securing means has a surface containing a plurality of hooks and the other of said securing means has a surface containing a plurality of loops. When the surfaces of these securing means are pressed into contact, the hooks interconnect with the loops to removably secure the skirt in place about the patient.

Crimped portions 13A and non-crimped portions 13B comprise a flexible waist band or section having elastic means disposed therein. During the process of showering, water may enter through the opening in the crimped portion of the waist band .to allow cleansing of body areas not normally connected to the dialysis bag; however, the non-crimped or flat portions of the waist band fits snugly about the patient's waist immediately over a see through pocket 14, disposed on the inside of the skirt by stitching or heat sealing means. Inside pocket 14 has a see-through flap or cover 15, disposed directly under the non-crimped or flat portion of the waist band and immediately above the flap over the pocket. The upper exterior portion of the inside pocket and the interior portion of the flap are provided with hook and loop or VELCRO ® fasteners 16A and 16B, so that, when these fasteners are pressed into contact to removably close the dialysis bag inside of the pocket, any water which may enter tangentially through the openings in the crimped portion of the waist band will be passed over the outside of the closed flap and thereby prevented from wetting or contaminating the bag. The non-crimped or flat portion of the waist band that fits snugly to the patient's abdomen, as shown in FIG. 1 prevents water from coming in contact with an uncovered stoma opening in the stomach region when the dialysis bag is removed from the opening and placed inside of the interior pocket in the skirt.

Figure 5:
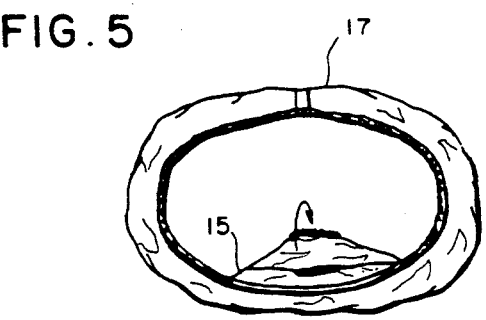
FIG. 5 is a top view of the dialysis bag protective skirt in the closed position showing the flap in the unclosed position.

In the FIG. 5 depiction, a top view of the dialysis bag protective skirt shows the juncture 17 or press fitted securing means 11 and 12 and an open flap 15 in the ready position to receive the bag containing the dialysis solution.

The protective skirt is preferably made of clear or see-through plastic and can also be effectively used to allow severely burned patients to shower non-burned areas without risk of bacterial infection to the burned areas of the body. If it is desired to prevent shower water from entering above the waist or upper area of the body, the entire waist band or uppermost section of the waterproof protective device can be made in a flat, non-crimped flexible configuration.

While the protective skirt of this invention has been described in its preferred embodiment, it is to be understood that many variations and alterations will be readily apparent to those skilled in the art, and that the illustrations herein contained are not by way of limitation and can be altered without departing from the scope of the invention.

I claim:

1. A skirt that permits a patient using a portable dialysis bag to shower without wetting said bag and to cleanse body areas inside and outside of the skirt that are not connected to the bag comprising: a waterproof skirt comprising a flexible waist band having crimped and non-crimped portions and having elastic means disposed therein;

securing means at overlapping portions of waist ends to hold said skirt in place about a patient's waist; and a pocket disposed on an inside part of said skirt to receive a portable dialysis bag;

wherein said pocket has a flap thereover to effect closure when hook and loop fasteners on an interior side of said flap and on an exterior side of said pocket are pressed into contact;

and wherein said non-crimped portion is flat and disposed above said flap.

2. The skirt of claim 1, made of see-through plastic.

3. The skirt of claim 1, wherein said securing means at overlapping portions of waist ends comprise interconnecting male and female fastening means.

4. The skirt of claim 3, wherein said interconnecting male and female fastening means comprises a plurality of hooks and a plurality of loops as fastening surfaces.

* * * * *